United States Patent [19]

Shigeyama et al.

[11] Patent Number: 5,450,204
[45] Date of Patent: Sep. 12, 1995

[54] INSPECTING DEVICE FOR INSPECTING PRINTED STATE OF CREAM SOLDER

[75] Inventors: Yoshihide Shigeyama; Nobuaki Kakimori; Yuichi Yamamoto; Yutaka Iwata; Kengo Nishigaki; Shin Kishimoto, Osaka, all of Japan

[73] Assignee: Sharp Kabushiki Kaisha, Osaka, Japan

[21] Appl. No.: 37,358

[22] Filed: Mar. 26, 1993

[30] Foreign Application Priority Data

Mar. 30, 1992 [JP] Japan ................... 4-074496

[51] Int. Cl.⁶ .............. G01B 11/24; G01B 11/28; G01B 11/14
[52] U.S. Cl. .................. 356/378; 356/375; 356/380; 356/381; 356/394
[58] Field of Search ............... 356/376, 237, 375, 379, 356/380, 381, 394

[56] References Cited

U.S. PATENT DOCUMENTS

| | | | |
|---|---|---|---|
| 3,627,427 | 12/1971 | Johnson et al. | 356/376 |
| 4,212,073 | 7/1980 | Balasubramanian | 364/562 |
| 4,641,972 | 2/1987 | Halioua et al. | 356/376 |
| 4,794,550 | 12/1988 | Greivenkamp, Jr. | 356/376 |
| 4,984,893 | 1/1991 | Lange | 356/376 |
| 5,064,291 | 11/1991 | Reiser | 356/376 |
| 5,069,548 | 12/1991 | Boehnlein | 356/376 |
| 5,088,828 | 2/1992 | Doemens et al. | 356/376 |
| 5,103,105 | 4/1992 | Ikegaya et al. | 356/376 |
| 5,118,192 | 6/1992 | Chen et al. | 356/376 |
| 5,166,753 | 11/1992 | Tokura | 356/376 |
| 5,192,983 | 3/1993 | Tokura | 356/376 |
| 5,202,749 | 4/1993 | Pfister | 356/376 |
| 5,206,705 | 4/1993 | Tokura | 356/376 |
| 5,267,217 | 11/1993 | Tokura et al. | 356/376 |
| 5,298,977 | 3/1994 | Shintani et al. | 356/376 |
| 5,307,151 | 4/1994 | Hof et al. | 356/376 |
| 5,307,152 | 4/1994 | Boehnlein et al. | 356/376 |

FOREIGN PATENT DOCUMENTS 3274404 12/1991 Japan .

Primary Examiner—Rolf Hille
Assistant Examiner—David Ostrowski

[57] ABSTRACT

An inspecting device inspects the printed state of cream solder by projecting a plurality of light patterns varying in phase onto a printed circuit board printed with cream solder, and processing signals obtained by an image pick-up device for picking up the image on the surface of the printed circuit board using a phase shifting method. A printed position, area, thickness or amount of the cream solder can be detected. By comparing the data thus obtained with reference data, the printed state is evaluated. The printed state of the cream solder may be examined quickly and positively, while a continuous automatic processing can be effected without stopping the mounting process of the printed circuit board in a production line.

19 Claims, 8 Drawing Sheets

INSPECTING DEVICE FOR INSPECTING PRINTED STATE OF CREAM SOLDER

BACKGROUND OF THE INVENTION

1. Field of the Invention

The present invention generally relates to an inspecting or examining device, and more particularly, to an inspecting device for inspecting printed state of cream solder printed on a printed circuit board for mounting thereon, at high density, very small electronic parts (1005 square chip and the like), narrow lead pitch IC, etc., as employed in headphone stereophonic appliances, cordless telephones, video cameras and the like.

2. Description of the Related Art

In the case where mounting of electronic parts onto the surface of a printed circuit board is to be automated, it is normally so arranged to print the cream solder on each specific position on a printed circuit board, and then, to temporarily fix the electronic parts on said printed circuit board by viscosity of the cream solder for subsequent soldering through a reflow furnace. Thus, it has been conventional practice to check the state of soldering of the printed circuit board after completion of the soldering process by the reflow furnace. However, due to the requirement for mounting at a higher density onto the printed circuit board, electronic parts to be soldered at the reverse face side, for example, LSI (large scale integrated circuit) having J leads, etc. have come into actual use, and in this case, it becomes difficult to effect inspection after completion of soldering. Moreover, the state of soldering of such electronic parts is largely affected by the state of printing when the cream solder is printed on the printed circuit board. Therefore, it becomes necessary to examine the printed state of the cream solder before the soldering process by the reflow furnace, and for this purpose, inspectors were distributed for effecting visual inspection.

However, such visual examination by the inspectors tends to increase the burden for the inspection, with a low working efficiency.

For examining the printed state of the cream solder, there has been conventionally employed an inspecting device arranged to project slit light onto a printed circuit board for picking up or photographing the projected pattern, so as to judge defects of soldering, positional deviation, etc. from the image signal obtained thereby. The known inspecting method based on the slit light projection as referred to above is higher in a detecting resolution as the interval for the slit light becomes small, while the detection speed is higher as the interval becomes large. In other words, accuracy and speed are in a perfect trade-off relation, and furthermore, there is such a disadvantage that, in the above inspecting method by the slit light projection, the coordinate values are available only on the slit.

Additionally, in the case where the deviation amount of the slit light, depending on a three-dimensional configuration of the plane to be measured, is detected, since one-slit tends to overlap a neighboring slit in some cases, a correct deviation amount can not be obtained. Thus, effecting retry or some countermeasures in spatial coding such as coloring the slit, etc. are required. Accordingly, in the conventional printed state inspecting device, there has been a limit to the improvement of accuracy, and reduction of measuring time.

SUMMARY OF THE INVENTION

Accordingly, an essential object of the present invention is to provide an inspecting device for inspecting a printed position, area, thickness or amount of cream solder printed on a printed circuit board, based on a plurality of image signals by projecting a plurality of phase-shifting light patterns onto the printed circuit board.

Another object of the present invention is to provide an inspecting device of the above described type which is capable of rapidly and correctly inspecting the printed state of the cream solder by comparing the above detected data with predetermined reference data.

In accomplishing these and other objects, according to one aspect of the present invention, there is provided an inspecting device for inspecting a printed position, area, thickness or amount of cream solder printed on a printed circuit board. The inspecting device includes a projection means for projecting a plurality of phase-shifting light patterns onto the printed circuit board from slantwise above, an image pick-up means disposed above said printed circuit board, and means for obtaining the position, area, thickness or amount of the cream solder printed on the printed circuit board by a plurality of image signals based on the plurality of phase-shifting light patterns outputted from said image pick-up means.

In another aspect of the present invention, the inspecting device further includes means for judging the printed state by comparing the data related to the position, area, thickness or amount of the cream solder obtained by said image signals, with predetermined reference data for the printed position, area, thickness or amount of the cream solder.

The light patterns shifting in phase as described above are characterized in that they are in stripe patterns, with the intensity thereof varying in a sine wave form. Meanwhile, the projecting means is characterized in the formation of a plurality of phase-shifting light patterns by a liquid crystal optical shutter having liquid crystal as a substantial grating. Moreover, the predetermined reference data for the printed state of the cream solder used for the above comparison is characterized in that it is obtained from a converting means which automatically produces an inspection data file by downloading CAD (computer aided design) data from a host computer preparing the CAD data for a screen mask of a screen printing machine which prints the cream solder, with a memory means for storing the inspection data being provided.

According to the inspecting device of the present invention as described above, since it is so arranged to project a plurality of phase-shifting light patterns onto the printed circuit board so as to use a plurality of phase-shifting image data, the entire surface of the printed circuit board can be rapidly inspected with high accuracy.

BRIEF DESCRIPTION OF THE DRAWINGS

These and other objects and features of the present invention will become apparent from the following description taken in conjunction with the preferred embodiment thereof with reference to the accompanying drawings, in which.

DETAILED DESCRIPTION OF THE INVENTION

Figure 1:
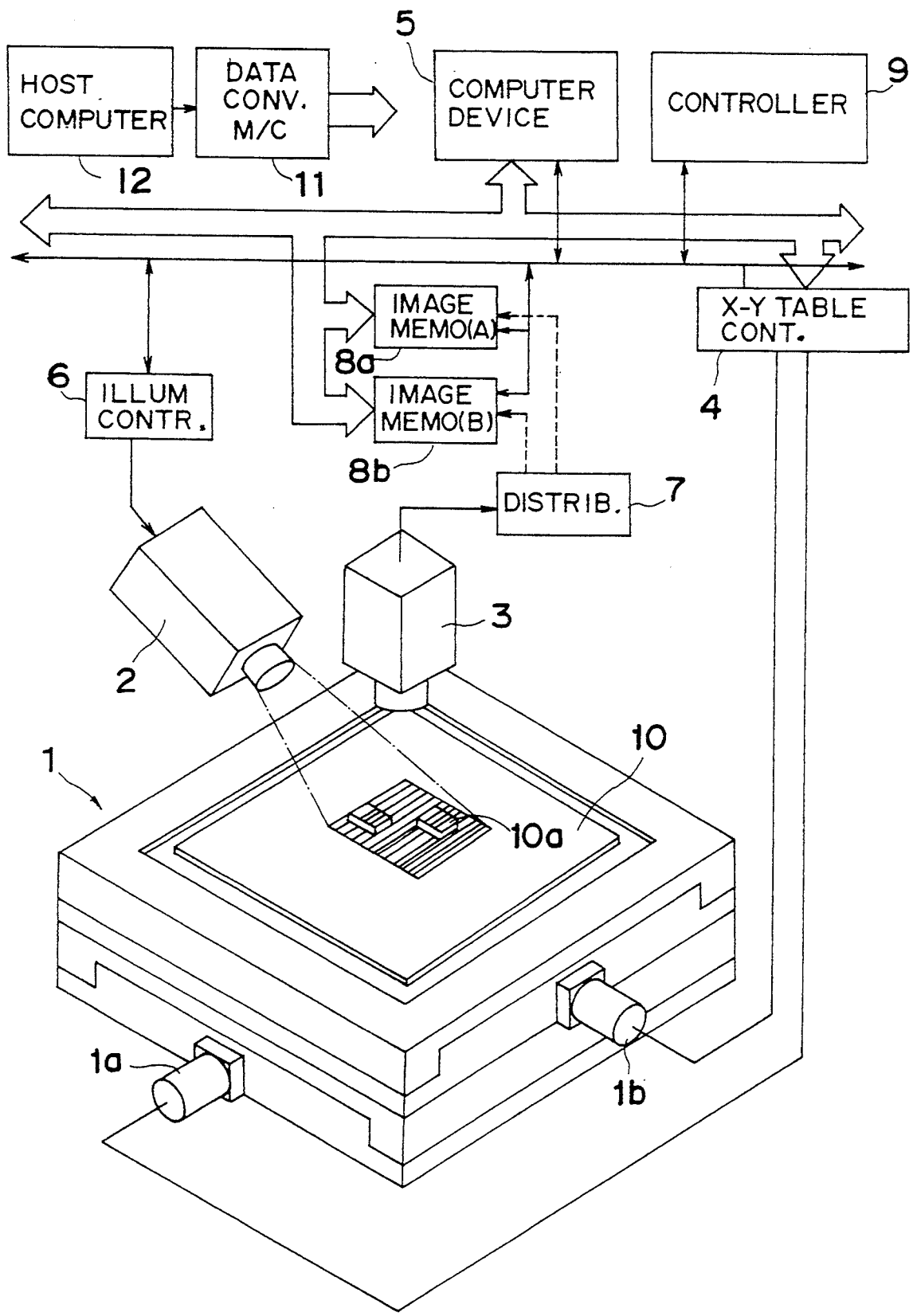
FIG. 1 is a perspective view, with a block diagram in part, showing an overall construction of a printed state inspecting device according to one preferred embodiment of the present invention.

Before the description of the present invention proceeds, it is to be noted that like parts are designated by like reference numerals throughout the accompanying drawings.

Referring now to the drawings, there is shown in FIG. 1, a printed state inspecting device according to one preferred embodiment of the present invention, which generally includes an X-Y table 1 for placing a printed circuit board 10 thereon, a projecting means i.e. illumination unit 2 (liquid crystal optical shutter) for projecting a plurality of slit-like phase-shifting light patterns onto the printed circuit board 10 from slantwise above (i.e., at an acute angle), and a CCD (charge coupled device) camera 3 for picking-up image of the printed circuit board 10 in a direction generally perpendicular to the surface of said printed circuit board 10. On the printed circuit board 10, cream solder 10a is printed to form a predetermined pattern. The X-Y table 1 is so arranged to displace the printed circuit board 10 placed thereon to any position in X-Y directions by driving pulse motors 1a and 1b through an X-Y table controller 4, based on instructions from a computer device 5 and a controller 9. An illumination controller 6, based on instructions from the controller 9, controls the projecting means or illumination unit 2 to project light phase-shifting by ¼ pitch onto the printed circuit board from slantwise above, and directs the illumination unit 2 to project stripe-shaped patterns whose illuminance varies in a sine wave form along the X or Y direction, onto the printed circuit board 10. The illumination unit 2 produces the striped-shape patterns through irradiating of light from the light source via a liquid crystal optical shutter. Moreover, these stripe-shaped patterns produce stripe-shaped patterns whose phase is shifted by ¼ pitch in the Y or X direction as described above by displacing the phase thereof as desired by controlling the liquid crystal optical shutter.

Figure 2:
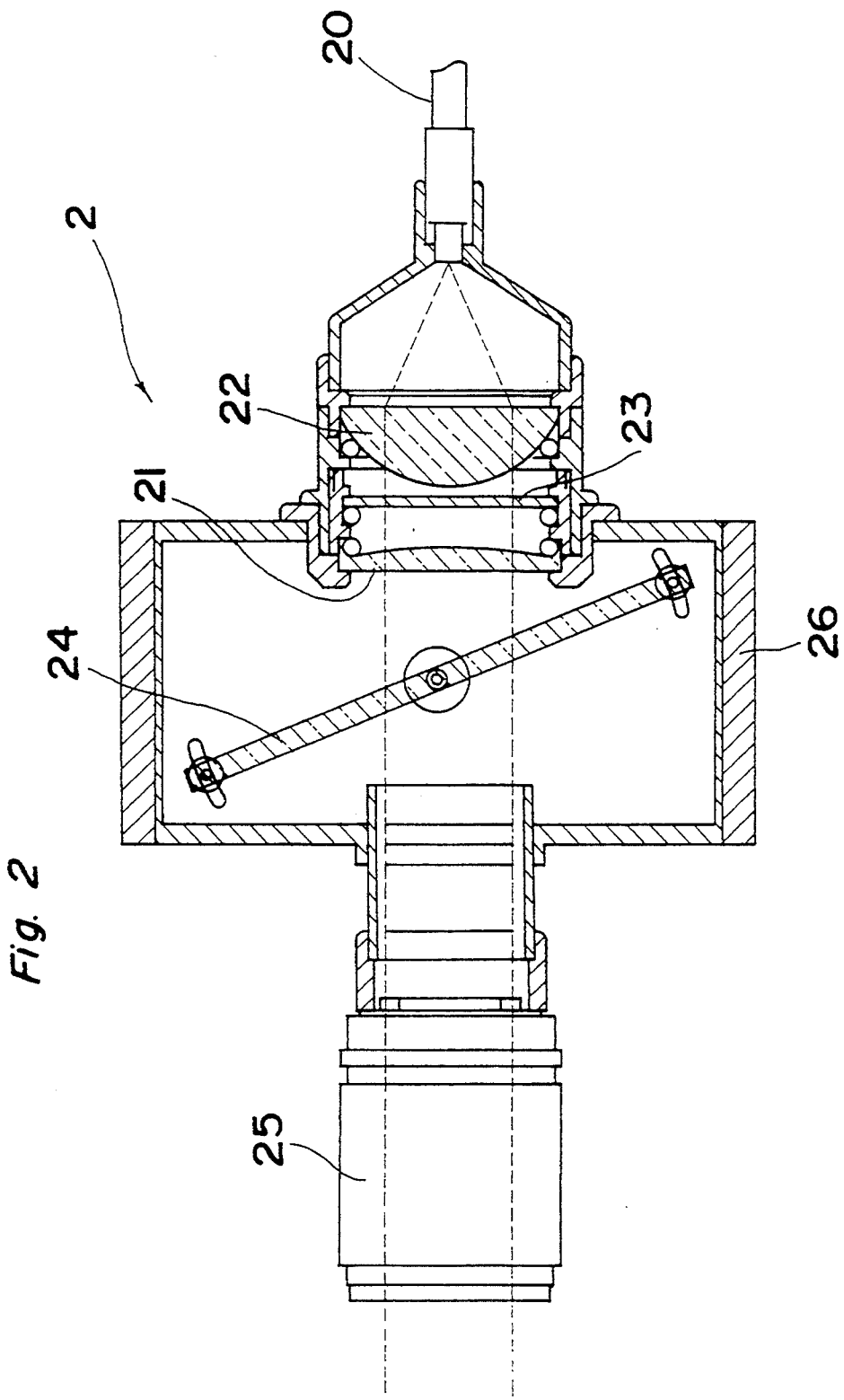
FIG. 2 is a side sectional view showing, on an enlarged scale, one embodiment of an illumination unit or projecting medians (liquid crystal optical shutter) employed n the arrangement of FIG. 1.

FIG. 2 shows a side sectional view of the illumination unit 2 as the projecting means which may be used in the inspecting device of FIG. 1.

In FIG. 2, light from a light source (not shown) is led by optical fibers 20, into condenser lenses 21 and 22, between which a filter 23 is inserted, and is turned into parallel light by said lenses 21 and 22 so as to be further led into a projecting lens 25 through a liquid crystal element 24. In this embodiment, a constant temperature control device 26 is provided between the condenser lenses 21 and 22 and the projecting lens 25, and the liquid crystal element 24 is disposed in said constant temperature control device 26. By this arrangement, drift in temperature of the liquid crystal element 24 is prevented, and the contrast of the projected patterns may be stabilized. Owing to the fact that the illumination unit 2 is disposed above the printed circuit board at an acute angle with respect to the printed circuit board 10 (FIG. 1), the focal distance of the projecting lens 25 is not the same at all portions on the printed circuit board 10, and in order to compensate for this disadvantage, the unit is provided diagonally with respect to an optical axis so as to allow adjustment of angles with respect to the optical axis.

Figure 3:
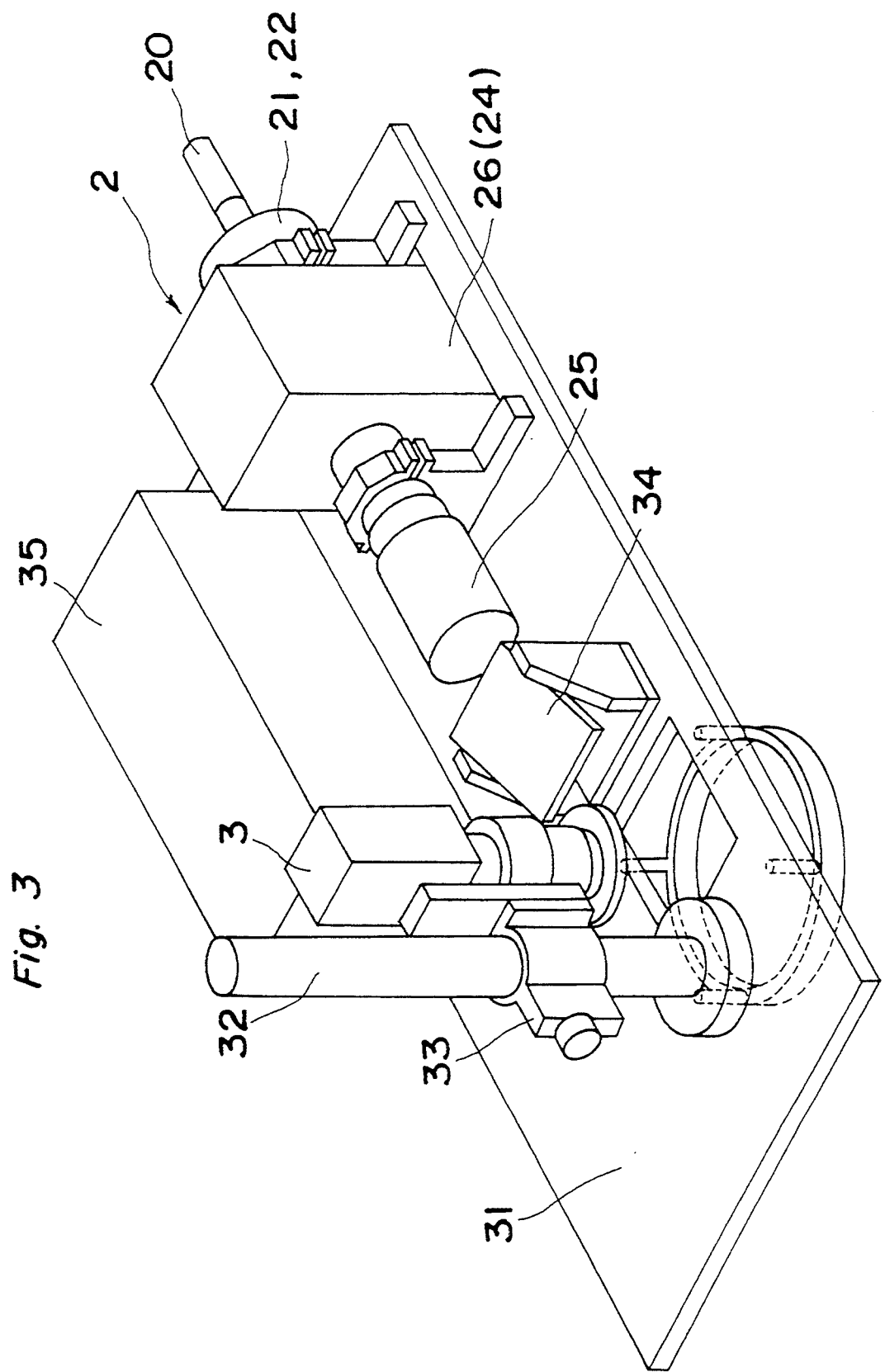
FIG. 3 is a perspective view showing a construction of an optical system employing the illumination unit of FIG. 2.

As a perspective view, FIG. 3 shows a specific positional relation between the illumination unit 2 and the CCD camera 3 referred to earlier, on an optical system chassis 31. A camera stand 32, to which the CCD camera 3 is fixed through a stand carrier 33, is mounted on optical system chassis 31. The illumination unit 2 including the optical fibers 20, condenser lenses 21 and 22, constant temperature control device 26 incorporated with the liquid crystal element 24, and the projection lens 25, etc. as described earlier with reference to FIG. 2, is also mounted on optical chassis 31 with the light therefrom being directed onto the printed circuit board by a deflection mirror 34. A controller 35 for the liquid crystal element 24 is also mounted on said chassis 31.

Figure 4:
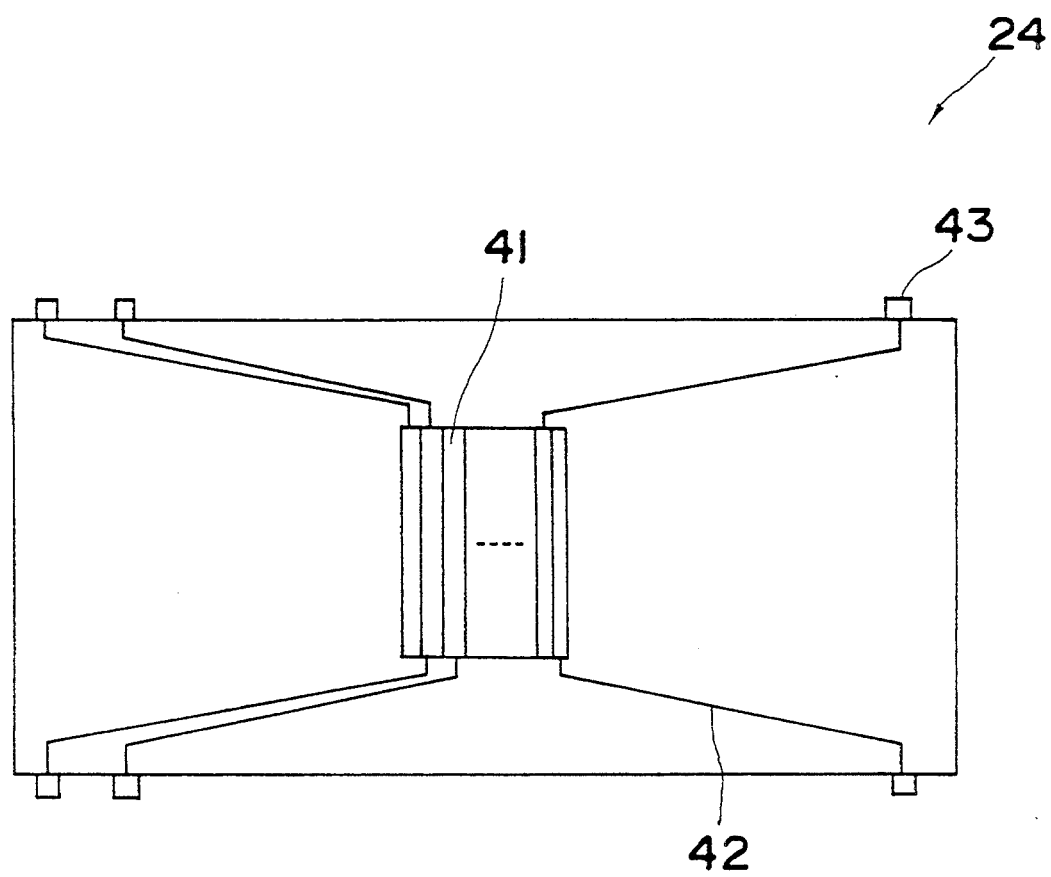
FIG. 4 is a diagram showing an example of a liquid crystal device employed in the illumination unit of FIG. 2, FIGS. 5(a) to 5(d) are diagrams for explaining a driving method of the liquid crystal of FIG. 4.
Figure 5A:
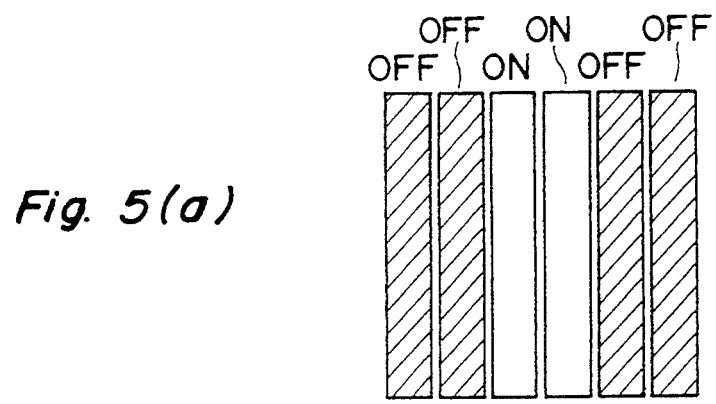
Figure 5B:
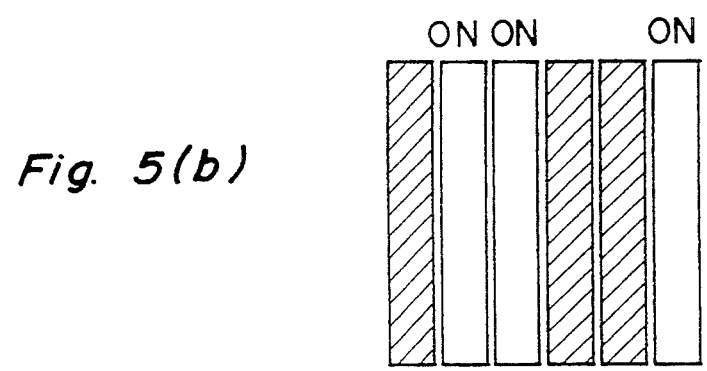
Figure 5C:
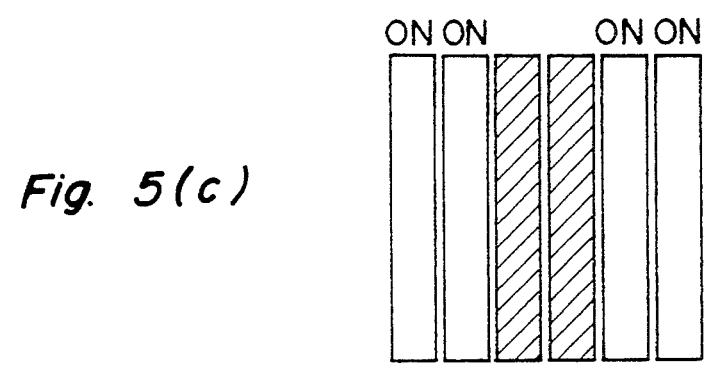
Figure 5D:
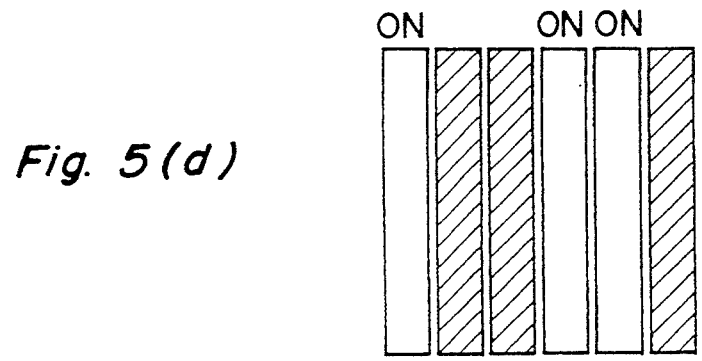

Referring to FIG. 4, there is shown the construction of the liquid crystal element 24, in which one transparent electrode thereof is provided on an entire surface, while the other transparent electrode is constituted by strip shaped electrode 41 divided into thin and long portions in one direction as shown. From the electrode portions of the strip electrodes 41, terminals 43 are led out through connecting lines 42. For the liquid crystal element 24, twist nematic type liquid crystal is employed, with polarizing plates (not shown) being applied to front and rear portions of the liquid crystal element 24.

Referring further to FIGS. 5(a) to 5(d), there is shown a method of driving the liquid crystal element 24. In this driving method, the electrode portions of the strip electrode 41 are driven so as to be shifted by ¼ pitch, thus producing light patterns varying in four phases. More specifically, as shown in FIGS. 5(a), 5(b), 5(c) and 5(d), the liquid crystal element 24 is driven so that each set of two electrode portions of the strip electrodes 41 are successively turned ON to transmit light. The periods of the shift, directions and the number of division of the strip electrodes, etc. may be set as desired according to the driving circuit.

By the employment of the liquid crystal optical shutter for the illumination unit 2, advantages as follows may be obtained.

In the first place, owing to the light transmitting characteristics of the liquid crystal, a stripe pattern having illuminance close to an ideal sine wave is obtained when prepared, whereby the measuring resolution for three-dimensional measurement can be improved. Secondly, since control of the phase shift of the stripe pattern may be effected electrically, it becomes possible to make the optical system compact in size, and also, to effect correct phase shift at high speed. Furthermore, in the arrangement of the printed state inspecting device of the present embodiment, the system construction may be simplified for reduction in size of the entire device, while the concept of the present invention plays an important role for providing a high speed inspecting device capable of functioning as an line type device.

The printed state inspecting device as described so far functions in a manner as follows.

When the printed circuit board 10 is placed on the X-Y table 1, the computer device 5 first sends an instruction signal to the X-Y table controller 4 together with data such as amount of displacement, etc., so as to move the printed circuit board 10 to a first inspection area (initial position). Such inspection area has been preliminarily set by dividing the printed circuit board 10 in advance, for example, by making the size of a visual field of the CCD camera 3 as a unit. Then, the controller 9 sends an instruction signal to the illumination controller 6 together with data such as the stripe pattern, etc., thereby causing the illumination unit 2 to start the illumination of the stripe pattern, and also, to successively change-over the four kinds of illumination by shifting the phase of this stripe pattern by ¼ pitch as shown in FIGS. 5(a) to 5(d). While the illumination for shifting the phase of the strip pattern is effected, the CCD camera 3 picks up the image of the inspection area for each illumination, and successively outputs image signals for the four images.

Figure 6:
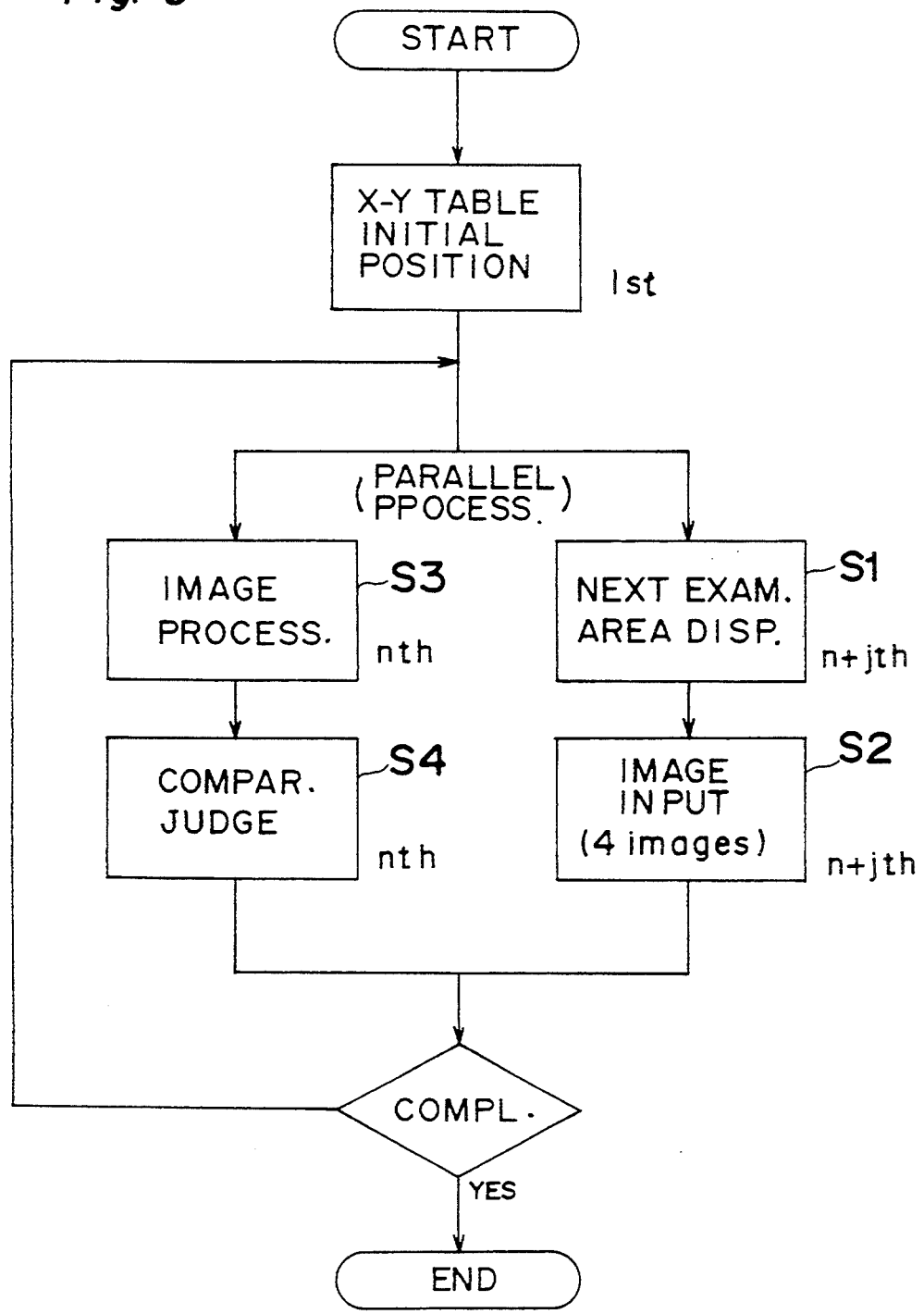
FIG. 6 is a flow-chart for explaining functioning of the systems arrangement of FIG. 1, FIGS. 7(a) to 7(d) are diagrams respectively showing images memorized by image memory for four image faces obtained through driving of the liquid crystal of FIG. 5, and FIGS. 8(a) to 8(e) are diagrams for explaining the phase-shifting method (stripe scanning method) employed in the present invention.
Figure 7A:
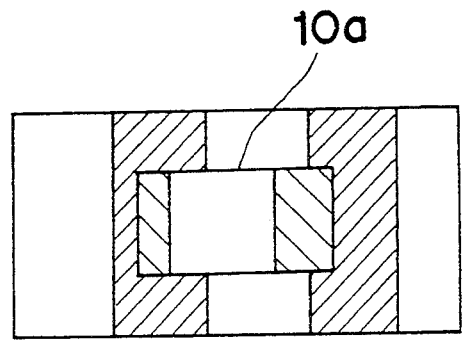
Figure 7B:
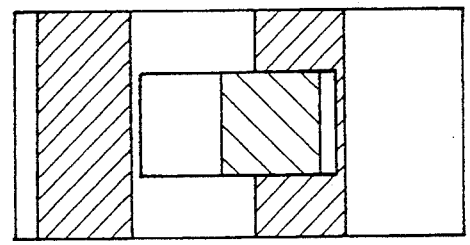
Figure 7C:
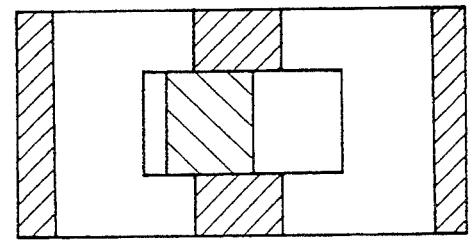
Figure 7D:
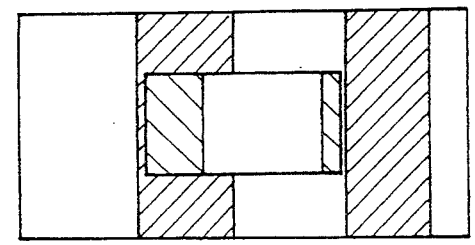

In FIG. 1, an image memory 8a is adapted to successively memorize the image signals for the four image sent through a distributor 7 coupled to the CCD camera 3, and the image signals thus memorized are applied to the computer device 5 connected therewith. While the computer device 5 processes the images thus stored in the image memory 8a, the X-Y table 1 is displaced to a subsequent inspection area, and the distributor 7 stores the inspected image in another image memory 8b. On the other hand, upon completion of the image processing of the memory 8a, since the next image signal has already been inputted to the memory 8b, the computer device 5 can immediately process the next image. In other words, as shown in FIG. 6, the inspection is effected in such a manner that: on one hand, at Step S1, displacement to the next inspection area (n+jth)→at Step S2, image input are effected, and on the other hand, at Step S3, nth image processing—at Step S4, comparative judgement are conducted by parallel processings. Subsequently, similar parallel processings are alternately repeated until the inspection for all the inspection areas is completed. As a result, according to the printed state inspecting device of the above embodiment, the printed state of the cream solder 10a on the printed circuit board 10 can be examined positively at high speed by successively processing the images, while moving in the inspection area under the control of the computer device 5 and the controller 9.

Subsequently, the image processing and the comparative judgement to be effected by the computer device 5 will be described hereinbelow.

The images in the inspection area when the phase of the stripe pattern is shifted by ¼ pitch will be as shown in FIGS. 7(a), 7(b), 7(c) and 7(d). As is clear from FIGS. 7(a) to 7(d), the stripe pattern projected onto the printed circuit board 10 is formed with deviation in the phase depending on a difference in height between the surface of the printed circuit board and the cream solder 10a. Therefore, in the computer device 5, based on the image signals of the four image faces, the heights of reflecting faces at respective parts within the inspection area are calculated by the phase shift method (stripe scanning method).

Figure 8:
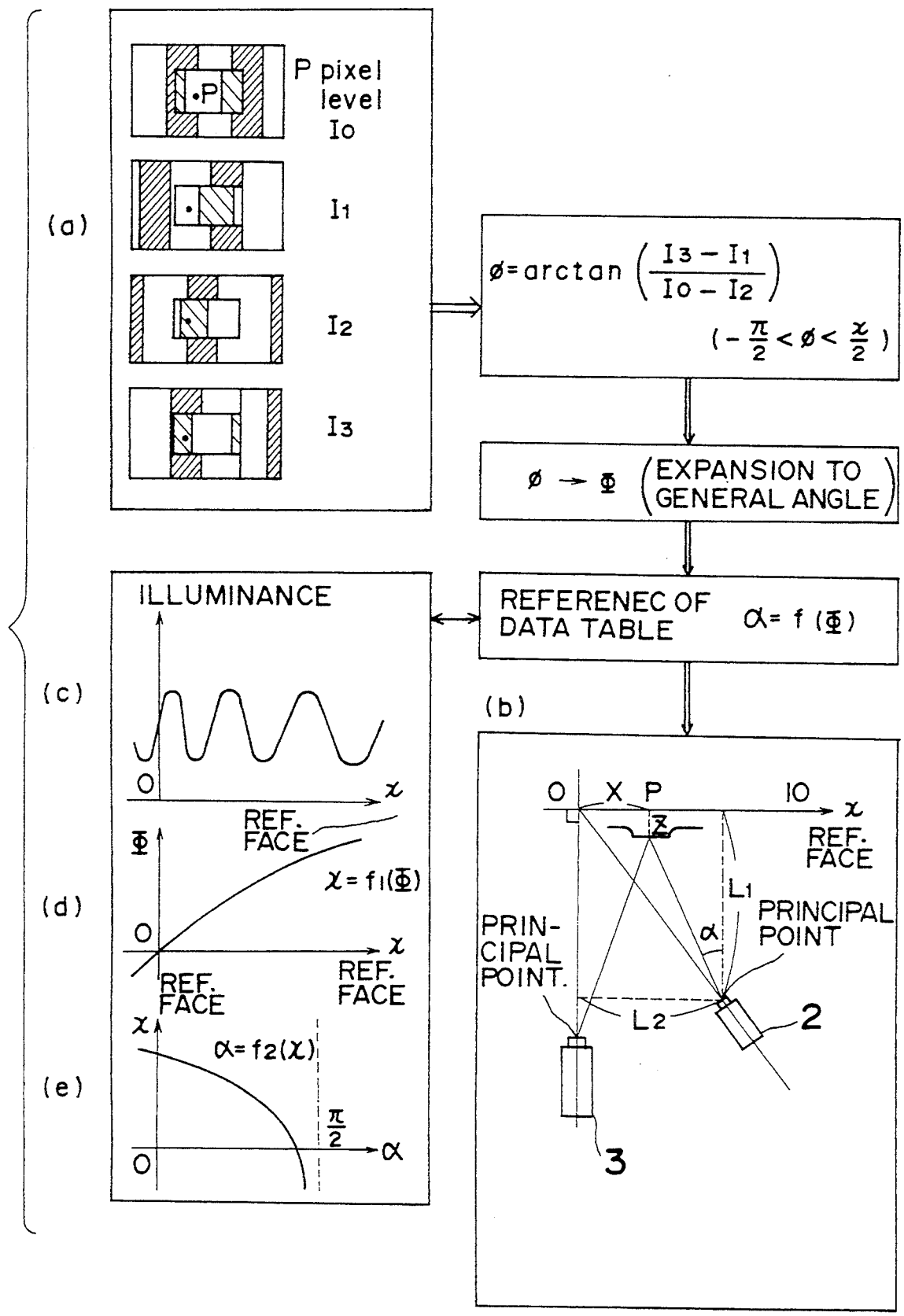

The measuring procedures are based on data flow as shown in FIG. 8, in which P represents arbitrary pixel within the inspection area, I0 to I3 show light intensity signal levels quantized to eight bits with respect to the respective pixels for the four image faces in FIGS. 7(a) to 7(d) at the pixel P, and Z denotes the height to be obtained for said pixel P. The data table for 1:1 function for $\alpha$ and $\phi$ is one preliminarily obtained on a reference surface of an optical conception diagram. More specifically, for the four light intensity signals, the light intensity signal of the phase $\phi$ is obtained with respect to $-\pi/2 < \phi < \pi/2$ from a following equation (1).

$$\phi = \arctan \frac{I3 - I1}{I0 - I2} \tag{1}$$

Subsequently, the light intensity signal of the phase is expanded into a general angle $\Phi$.

Here, as shown in FIG. 8(b), the CCD camera 3 is disposed in a perpendicular direction from an original point 0 at a center of image pick-up, with respect to the reference face on the surface of the printed circuit board 10, with the illumination unit 2 being directed at an acute angle with respect thereto. Thus, illuminance I in the x direction on the surface of the printed circuit board 10 is subjected to phase-shift as shown in FIG. 8(c). This phase-shift $\Phi$ is represented by a following function with respect to the x direction as shown in FIG. 8(d).

$$x = f_1(\Phi) \tag{2}$$

Meanwhile, the angle $\alpha$ of the illumination unit 2 with respect to the vertical axis on the surface of the printed circuit board is represented by a following equation in the x direction (FIG. 8(e)).

$$\alpha = f_2(x) \tag{3}$$

From the above equations (2) and (3), another equation is obtained as follows.

$$\alpha = f(\Phi) \tag{4}$$

The data table for the 1:1 function of $\alpha$ and $\Phi$ is preliminarily obtained on the reference surface of the optical conception diagram and memorized. Thus, height data Z in the pixel unit is obtained by a following equation.

$$Z = L1 - \frac{L2}{\tan \alpha} + \frac{X}{\tan \alpha} \tag{5}$$

The height data thus obtained is in the pixel unit of the picked-up image, and is stored in the memory of the computer device 5 as a distance image.

Moreover, based on the height data at the respective portions, the range occupied by the printed region of the cream solder 10a higher than the surface of the printed circuit board is detected to find the position and area. Then, by integrating the heights at the respective portions within this range, the amount of the printed solder is calculated. Subsequently, by comparing the data for the position, area, height or amount of the printed solder thus obtained, with the reference data preliminarily memorized, the printed state of the cream solder 10a in said inspection area is judged depending on whether or not the results of comparison are within an allowable range. For the above reference data, for example, data obtained by subjecting a good printed circuit board to similar treatments, and preliminarily memorized in ROM or the like within the computer device 5 may be employed. However, it is more efficient to use an inspection data set with the judging standards as obtained through automatic conversion into various data sued such as by down-loading CAD (computer aided design) data from the host computer 12 and converting the CAD data of the screen mask of a screen printing machine for printing the cream solder using a data conversion machine 11.

As described so far, in the present invention, relative heights of the cream solder are detected by the phase shift method based on the images obtained by deviating the phase of the stripe pattern.

As is clear from the foregoing description, according to the printed state inspecting device of the present invention, since it becomes possible to inspect the printed state of the cream solder rapidly and positively, continuous automatic processing for mounting onto the printed circuit boards in production lines can be effected without stopping the mounting step. Thanks to an accurate inspection, faulty soldering may be prevented in advance for improved productivity. Furthermore, since the height measuring accuracy may be determined as desired by the setting of the optical system, the inspecting device of the present invention can be utilized for cream solder pads of high density mounting parts such as 1005 square chips, 0.5 mm pitch QFP, etc. In the above case, with respect to the cream solder pad having a thickness of 150 μm, measurement at an accuracy of $\sigma = 3$ μm at standard deviation can be effected.

Although the present invention has been fully described by way of example with reference to the accompanying drawings, it is to be noted here that various changes and modifications will be apparent to those skilled in the art. Therefore, unless otherwise such changes and modifications depart from the scope of the present invention, they should be construed as included therein.

What is claimed is:

1. An inspecting device for inspecting a position, area, thickness or amount of cream solder printed on a printed circuit board, said inspecting device comprising:
   a projecting means for projecting a plurality of phase-shifting light patterns onto the printed circuit board, said phase-shifting light patterns being incident on said printed circuit board at an acute angle, said projecting means producing said phase-shifting light patterns using a liquid optical shutter having a liquid crystal element as a substantial grating;
   an image pick-up means for picking up images of a portion of said printed circuit board where said phase-shifting light patterns are incident, and generating image signals therefrom; and
   means for obtaining the position, area, thickness or amount of cream solder printed on the printed circuit board from said plurality of image signals.

2. An inspecting device as claimed in claim 1, wherein intensity of said phase-shifting light patterns varies in a sine wave form.

3. An inspecting device as claimed in claim 1, further including means for judging a printed state of cream solder on said printed circuit board by comparing data related to the position, area, thickness or amount of the cream solder, output by said means for obtaining, with predetermined reference data for the printed position, area, thickness or amount of the cream solder.

4. An inspecting device as claimed in claim 3, wherein said predetermined reference data for the printed position, area, thickness or amount of the cream solder is obtained from a converting means which automatically produces an inspection data file by down-loading CAD data from a host computer preparing the CAD data for a screen mask of a screen printing machine which prints the cream solder.

5. An inspecting device for inspecting a position, area, thickness, or amount of cream solder printed on a printed circuit board, said inspecting device comprising:
   an illumination unit projecting a plurality of phase-shifting light patterns onto said printed circuit board, said phase-shifting light patterns being incident on said printed circuit board at an acute angle, said illumination unit producing said phase-shifting light patterns using a liquid crystal optical shutter having a liquid crystal element as a substantial grating;
   an image pick-up device picking up images of a portion of said printed circuit board where said phase-shifting light patterns are incident, and generating a plurality of image signals based thereon; and
   a processor receiving said plurality of image signals from said image pick-up device, and obtaining the position, area, thickness, or amount of cream solder printed on said circuit board from said plurality of image signals.

6. An inspecting device as claimed in claim 5, wherein intensity of said phase-shifting light patterns varies in a sine wave form.

7. An inspecting device as claimed in claim 5, wherein said processor judges a printed state of cream solder on said printed circuit board by comparing data related to the position, area, thickness or amount of the cream solder with predetermined reference data for the printed position, area, thickness or amount of the cream solder.

8. An inspecting device as claimed in claim 7, wherein said predetermined reference data for the printed position, area, thickness or amount of the cream solder is obtained from a converter which automatically produces an inspection data file by down-loading CAD data from a host computer preparing the CAD data for a screen mask of a screen printing machine which prints the cream solder.

9. An inspecting device as claimed in claim 5, further comprising:
   a positioning device which positions said printed circuit board relative to said image pick-up device; and wherein
   said image pick-up device picks up an image of predetermined dimensions, said predetermined dimensions being smaller than dimensions of said printed circuit board; and
   said processor includes a first memory and a second memory, said first memory stores said plurality of image signals corresponding to a current printed circuit board portion of said predetermined dimensions, said processor obtaining the position, area, thickness or amount of cream solder printed on said current printed circuit board portion while said positioning device positions said printed circuit board in a new position and said second memory stores said plurality of image signals corresponding to a new printed circuit board portion of said predetermined dimensions.

10. A method of inspecting a position, area, thickness, or amount of cream solder printed on a printed circuit board, said method comprising the steps of:
   a) projecting a plurality of phase-shifting light patterns onto said printed circuit board using a liquid crystal optical shutter having a liquid crystal element as a substantial grating, said phase-shifting light patterns being incident on said printed circuit board at an acute angle;
   b) picking up images of a portion of said printed circuit board where said phase-shifting light patterns are incident, and generating image signals based thereon; and
   c) obtaining the position, area, thickness, or amount of cream solder printed on said circuit board from said plurality of image signals.

11. A method of inspecting as claimed in claim 10, wherein intensity of said phase-shifting light patterns varies in a sine wave form.

12. A method of inspecting as claimed in claim 10, further comprising the state of d) judging a printed state of cream solder on said printed circuit board by comparing data related to the position, area, thickness or amount of the cream solder, output by said step c), with predetermined reference data for the printed position, area, thickness or amount of the cream solder.

13. An inspecting device as claimed in claim 12, wherein said predetermined reference data for the printed position, area, thickness or amount of the cream solder is obtained by automatically producing an inspection data file by down-loading CAD data from a host computer preparing the CAD data for a screen mask of a screen printing machine which prints the cream solder.

14. An method of inspecting as claimed in claim 10, wherein
   said step b) picks up an image of predetermined dimensions, said predetermined dimensions being smaller than dimensions of said printed circuit board; and
   said step c) includes the steps of c1) storing, in a first memory, said plurality of image signals corresponding to a current printed circuit board portion of said predetermined dimensions, c2) obtaining the position, area, thickness or amount of cream solder printed on said current printed circuit board portion, and c3) simultaneous with said step c2), positioning said printed circuit board in a new position and storing, in a second memory, said plurality of image signals corresponding to a new printed circuit board portion of said predetermined dimensions.

15. An inspecting device as claimed in claim 1, wherein said projecting means includes a light source and a liquid crystal element, said light source projecting a light beam through said liquid crystal element, said liquid crystal element having a strip electrode, said strip electrode having electrode portions which are driven so as to shift the pitch thereof by one-quarter to produce four phase-shifting light patterns.

16. An inspecting device as claimed in claim 5, wherein said illumination unit includes a light source and a liquid crystal element, said light source projecting a light beam through said liquid crystal element, said liquid crystal element having a strip electrode, said strip electrode having electrode portions which are driven so as to shift the pitch thereof by one-quarter to produce four phase-shifting light patterns.

17. A method of inspecting as claimed in claim 10, wherein said step a) includes the steps of:
   a1) projecting a light beam through a liquid crystal element, said liquid crystal element having a strip electrode, said strip electrode having electrode portions; and
   a2) driving said electrode portions so as to shift the pitch thereof by one-quarter to produce four phase-shifting light patterns.

18. An inspecting device as claimed in claim 1, further comprising:
   a positioning means for positioning said printed circuit board relative to said image pick-up means; and wherein
   said image pick-up means picks up an image of predetermined dimensions, said predetermined dimensions being smaller than dimensions of said printed circuit board; and
   said means for obtaining includes a first memory means and a second memory means, said first memory means for storing said plurality of image signals corresponding to a current printed circuit board portion of said predetermined dimensions, said means for obtaining obtains the position, area, thickness or amount of cream solder printed on said current printed circuit board portion while said positioning means positions said printed circuit board in a new position and said second memory means stores said plurality of image signals corresponding to a new printed circuit board portion of said predetermined dimensions.

19. A method of inspecting as claimed in claim 10, further comprising the steps of:
   d) positioning said printed circuit board relative to an image pick-up device; and wherein
   said step b) picks up, using said image pick-up device, an image of predetermined dimensions, said predetermined dimensions being smaller than dimensions of said printed circuit board; and
   said step c) includes the steps of,
   c1) storing, in a first memory, said plurality of image signals corresponding to a current printed circuit board portion of said predetermined dimensions,
   c2) obtaining the position, area, thickness or amount of cream solder printed on said current printed circuit board portion while said printed circuit board is positioned in a new position, and
   c3) storing, in a second memory, said plurality of image signals corresponding to a new printed circuit board portion of said predetermined dimensions.

* * * * *